(12) United States Patent
Volodin

(10) Patent No.: US 8,673,068 B2
(45) Date of Patent: Mar. 18, 2014

(54) DEVICE FOR INACTIVATING AND FINELY FILTERING VIRUSES AND MICROORGANISMS IN A FLOW OF AIR

(75) Inventor: Alexei Mikhailovich Volodin, Moscow (RU)

(73) Assignees: Elena Vladimirovna Volodina, Moscow (RU); Alexandr Vladimirovich Nagolkin, Moscow (RU)

( * ) Notice: Subject to any disclaimer, the term of this patent is extended or adjusted under 35 U.S.C. 154(b) by 477 days.

(21) Appl. No.: 13/119,388

(22) PCT Filed: Sep. 18, 2008

(86) PCT No.: PCT/RU2008/000603
§ 371 (c)(1),
(2), (4) Date: May 24, 2011

(87) PCT Pub. No.: WO2010/033048
PCT Pub. Date: Mar. 25, 2010

(65) Prior Publication Data
US 2011/0209621 A1    Sep. 1, 2011

(51) Int. Cl.
*B03C 3/49* (2006.01)
(52) U.S. Cl.
USPC ............... 96/69; 55/DIG. 38; 96/76; 96/77; 96/97; 96/98
(58) Field of Classification Search
USPC ........... 96/61, 62, 66, 68–70, 75–77, 97–100; 55/DIG. 38; 422/122, 186.04
See application file for complete search history.

(56) References Cited

U.S. PATENT DOCUMENTS 4,244,710 A * 1/1981 Burger .............................. 95/69
4,689,056 A * 8/1987 Noguchi et al. .................. 96/79
(Continued)

FOREIGN PATENT DOCUMENTS

JP    6-238194 A  *  8/1994
JP    2002136585    5/2002
(Continued)

OTHER PUBLICATIONS

English Abstract of 2002136585 Published May 15, 2002.

*Primary Examiner* — Richard L Chiesa
(74) *Attorney, Agent, or Firm* — Ladas & Parry LLP

(57) ABSTRACT

This device for inactivating and finely filtering viruses and microorganisms in a flow of air is intended for cleaning air or gas. The device includes a high voltage power supply (4) and the following components arranged in series in the direction of flow: a unit (1) for pre-treating a flow of air, a two-section inactivation chamber (2) and a precipitator (3). The pre-treating unit (1) consists of oppositely charged conductive filtering elements (7, 7'). The first conductive filtering element (7) in the direction of flow is in the form of a cylindrical electrode (6) and a plate (9) which is made of a current conductive, highly porous material and is positioned at a distance from the free end face of the cylindrical electrode (6). A needle electrode (8), electrically associated with the plate (9), is adjacent to said plate. The base of the cylindrical electrode is in the form of a plate (7) which is made of a conductive, porous and permeable material and is adjacent to a plate (5) made of a dielectric, highly porous permeable material. The needle electrode is disposed coaxially with the cylindrical electrode and the point of the needle electrode is oriented towards the dielectric plate. The cylindrical and needle electrodes are connected to opposite poles of the power supply. The device makes it possible to increase the operational efficiency of the device.

20 Claims, 5 Drawing Sheets

(56) References Cited

U.S. PATENT DOCUMENTS

| | | | |
|---|---|---|---|
| 5,474,600 A * | 12/1995 | Volodina et al. | 96/57 |
| 5,695,549 A * | 12/1997 | Feldman et al. | 96/55 |
| 5,733,360 A * | 3/1998 | Feldman et al. | 95/78 |
| 5,951,742 A * | 9/1999 | Thwaites et al. | 95/57 |
| 6,506,238 B1 * | 1/2003 | Endo | 96/79 |
| 7,198,660 B2 * | 4/2007 | Billiotte et al. | 96/66 |
| 7,384,456 B2 * | 6/2008 | Aubert | 96/77 |
| 2007/0137480 A1 * | 6/2007 | Bergeron et al. | 95/79 |
| 2008/0170971 A1 * | 7/2008 | Bergeron et al. | 422/171 |

FOREIGN PATENT DOCUMENTS

| | | |
|---|---|---|
| RU | 2026751 C1 | 1/1995 |
| RU | 2286271 C1 | 10/2006 |

* cited by examiner

DEVICE FOR INACTIVATING AND FINELY FILTERING VIRUSES AND MICROORGANISMS IN A FLOW OF AIR

This application is the national stage of International Application No. PCT/RU2008/000603 filed on Sep. 18, 2008.

THE FIELD OF THE ART

The invention relates to cleaning air or a gas from microorganisms, viruses, solid and liquid aerosols and more specifically concerns an apparatus for the inactivation and fine filtration of viruses and microorganisms in an air flow.

THE PRIOR ART

An apparatus for the inactivation and fine filtration of viruses and microorganisms is known according to the patent RU 2026751, this apparatus comprising a high-voltage power supply and, in series along the flow, an air flow pretreatment means, a two-compartment inactivation chamber, and a precipitator, which is embodied as oppositely charged plates made of a high-porosity current-conductive material and arranged in parallel to each other, with plates made of a high-porosity insulating material arranged between the current-conductive plates. Herein, the air flow pretreatment means is formed of oppositely charged current-conductive filtering units, with a plate made of a permeable high-porosity insulating material installed between them, and each compartment of the two-compartment inactivation chamber is embodied as a needle corona electrode and a cylinder non-corona electrode, the two electrodes being arranged coaxially to each other and each being electrically connected to the relevant plate made of a current-conductive filtering material.

In this apparatus, the air-flow pretreatment means is a coarse filter unit for cleaning an air flow from suspended mechanical particles and practically does not affect the inactivation of viruses and microorganisms. In this connection, the entire burden of the inactivation proper falls on the inactivation chamber, thereby complicating the performance thereof and reducing the efficiency of the inactivation process.

The object of the invention is to create an apparatus for the inactivation and fine filtration of viruses and microorganisms in an air flow such that an air-flow pretreatment means in this apparatus, apart from scavenging mechanical particles from the flow, performs the preconditioning of bioaerosols that occur in the flow prior to inactivation, thereby providing the most favorable conditions for the operation of the inactivation chamber and precipitator downstream, an improvement of their design, and ultimately an enhancement of the efficiency of the apparatus as a whole.

DISCLOSURE OF THE INVENTION

The object is achieved as follows: in an apparatus for the inactivation and fine filtration of viruses and microorganisms in an air flow comprising a high-voltage power supply and, in series along the flow: an air flow pretreatment means formed of oppositely charged current-conductive filtering units with a plate made of a high-porosity permeable material installed between them; a two-compartment inactivation chamber, each compartment being embodied as a needle corona electrode and a cylinder non-corona electrode, the two electrodes being arranged coaxially to each other and each being electrically connected to the relevant plate made of a current-conductive filtering material; and a precipitator embodied as oppositely charged plates made of a high-porosity current-conductive material and arranged in parallel to each other, with plates made of a permeable high-porosity insulating material arranged between these plates, according to the present invention, at least the first (along the flow) current-conductive filtering unit of the air flow pretreatment means is embodied as a cylinder electrode having a base in the form of a plate made of a permeable high-porosity current-conductive material, this plate being adjacent to the plate made of a permeable high-porosity insulating material, and a plate which is made of a high-porosity current-conductive material and arranged at a distance from the free end of the cylinder electrode adjacent to the needle electrode that is electrically connected to this plate, is arranged coaxially to the cylinder electrode, and has its point directed toward the insulating plate, wherein the cylinder electrode and the needle electrode are connected to the opposite poles of the power supply.

Expediently, the two-compartment inactivation chamber is embodied as a single cylinder non-corona electrode inside which a partition made of a permeable high-porosity current-conductive material is installed across the flow. Herein, the needle corona electrodes of the first compartment and the second compartment of the inactivation chamber have the points thereof directed toward each other and the other ends electrically connected to plates made of a current-conductive filtering material, each plate being arranged opposite to the corresponding end face of the cylinder non-corona electrode. The needle corona electrodes of the first compartment and the second compartment of the inactivation chamber are electrically connected to each other and to the pole of the power supply that is opposite to the pole connected to the needle electrode of the pretreatment means.

The two-compartment inactivation chamber may be embodied in such a way that the needle corona electrodes of the first compartment and the second compartment of the two-compartment inactivation chamber are directed in opposite directions and installed coaxially to the corresponding cylinder electrodes on the opposite sides of the plate made of a current-conductive filtering material, this plate being arranged across the flow between the cylinder non-corona electrodes of the first compartment and the second compartment and being insulated from them, and the plates made of a current-conductive filtering material adjacent to the ends of the cylinder electrodes at the inlet and outlet of the inactivation chamber are electrically connected to each other and to the last (along the flow) current-conductive filtering plate of the pretreatment means, and the needle corona electrodes are electrically connected to the plate made of a current-conductive filtering material positioned in between these electrodes.

In another embodiment of the invention, the two-compartment inactivation chamber may be formed of two in-series arranged cylinder non-corona electrodes and a plate made of a current-conductive filtering material being adjacent to the first end (along the flow) of each of these electrodes, wherein the non-corona electrodes are connected to the opposite poles of the power supply and wherein the needle corona electrodes both have their points directed counterflow and are electrically connected so that the needle electrode of the first compartment is connected to the current-conductive plate that is adjacent to the cylinder electrode of the second compartment and the needle electrode of the second compartment of the inactivation chamber is connected to the plate made of a current-conductive filtering material that is positioned directly following this electrode.

It is desirable to install a plate made of an insulating filtering material between the second filtering unit (along the flow) of the air flow pretreatment means and the first compartment of the inactivation chamber.

In a preferred embodiment, the apparatus further comprises at least one more two-compartment inactivation chamber that is an analogue of the first chamber but has the opposite polarity of electrode connection, this chamber being installed in series to the first chamber along the flow, with the direction of the needle corona electrodes of each next inactivation chamber being identical or opposite to the direction of the needle electrodes of the previous chamber.

It is desirable to install a plate made of a high-porosity insulating material between neighboring current-conductive filtering plates of the previous inactivation chamber and the next inactivation chamber.

Further, a needle electrode may be electrically connected to the first (along the flow) current-conductive plate of the precipitator, this needle electrode having its point directed counterflow, wherein a cylinder non-corona electrode is installed coaxially to this needle electrode with a plate made of a current-conductive filtering material being positioned adjacent to the front end (along the flow) of the cylinder electrode, this plate being electrically connected to the needle electrode of the last inactivation chamber along the flow.

To the first (along the flow) current-conductive plate of the precipitator, a cylinder electrode may be connected by one end, and opposite to the other end of this cylinder electrode, one more plate made of a current-conductive filtering material may be installed across the flow, wherein a needle corona electrode positioned coaxially to the cylinder electrode is electrically connected to this plate, has its point directed along the flow, and is connected to the pole of the power supply opposite to the pole connected to the needle electrode of the last compartment (along the flow) of the inactivation chamber.

For leveling the flow concentrations of particles to be precipitated, ozone, or ions, it is desirable to equip the apparatus with at least one flow turbulizer.

It is advisable to install the turbulizer upstream to the precipitator.

Further, it is desirable to equip at least one of the current-conductive plates of the precipitator and/or the turbulizer with a coating capable of providing the decomposition of ozone, nitrogen oxide, and/or other harmful gases.

The material whereof the insulating filtering plates are made may contain a catalyst for catalyzing the decomposition of ozone, nitrogen oxides, and/or harmful gases.

In a preferred embodiment, the needle corona electrode is embodied as a wire installed inside a metallic pipe coaxially thereto and protruding therefrom.

It is also desirable to connect at least some of the corona electrodes to the power supply via a resistor the resistance whereof is selected from the limit imposed on the peak consumption current value for the set voltage.

In one more preferred embodiment, the power supply is voltage stabilized, can maintain the consumption current within the set range, and can automatically switch itself from voltage stabilization to current stabilization once a set value of the consumed current is reached.

It is expedient to make current-conductive plates in the precipitator of a foamed metal and arrange them so that the distance between them decreases along the air flow, and to make the insulating filtering plates of the precipitator of foamed polyurethane and install them in an order such that the cell size of the material of the plates decreases along the air flow. Further, the current-conductive plates of the precipitator may be made of a foamed metal coated with an insulating coating.

The invention will be further illustrated by means of description of particular embodiments and drawings.

EMBODIMENTS OF THE INVENTION

Figure 1:
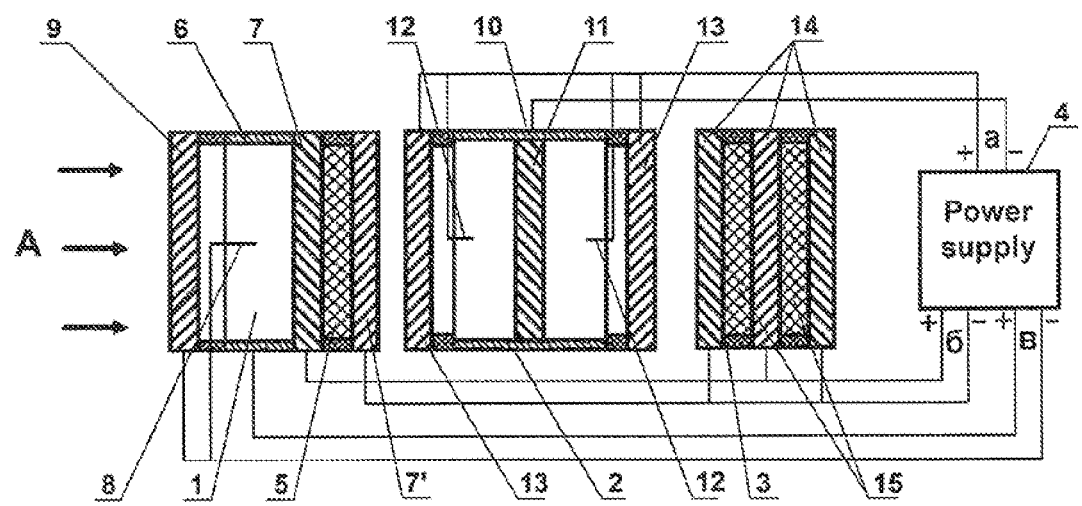
FIG. 1 schematically shows a section of the apparatus for the inactivation and fine filtration of viruses and microorganisms in an air flow according to the present invention.

The apparatus for the inactivation and fine filtration of viruses and microorganisms in an air flow as shown in FIG. 1 comprises an air flow pretreatment means 1, a two-compartment inactivation chamber 2, and a precipitator 3, all the three being arranged in series along the air flow A and connected to a high-voltage direct-current power supply 4. The air flow pretreatment means 1 contains a first current-conductive filtering unit and a second current-conductive filtering unit 7 and 7', respectively, charged oppositely to each other, and a plate 5 made of a permeable high-porosity insulating material, for example, of open-cell foamed polyurethane, positioned between the filtering units. At least the first current-conductive filtering unit (along the flow A) in this embodiment is embodied as a cylinder electrode 6 having a planar porous base 7 which is adjacent to the plate 5, and a needle corona electrode 8 is arranged coaxially to the cylinder electrode 6 on the side of the front end thereof, the needle corona electrode 8 having its point directed toward the insulating plate 5. In front of the electrode 8, there is a plate 9 made of a high-porosity current-conductive material, for example, foamed nickel, positioned at a small distance from the electrode 8 and electrically connected thereto.

The two-compartment inactivation chamber 2 in this embodiment is embodied as a single cylinder non-corona electrode 10, wherein a flow-shutting partition 11 made of a permeable high-porosity current-conductive material, for example, of foamed nickel, is installed in the middle of the cylinder electrode across the flow. The needle corona electrodes 12 of the first compartment and the second compartment have their points directed towards each other and are electrically connected to each other and to plates 13 which are made of a permeable high-porosity current-conductive material and are installed so that there is one plate at each end of the cylinder electrode 10. Herein, the potential of the plates 13 is opposite to the potential of the needle electrode 8 of the pretreatment means 1.

The precipitator 3 contains three plates 14 made of a high-porosity current-conductive material, installed in parallel to each other across the flow A, and connected alternately to the opposite poles of the power supply 4. Between the plates 14, there are plates 15 made of a permeable high-porosity insulating material.

Figure 2:
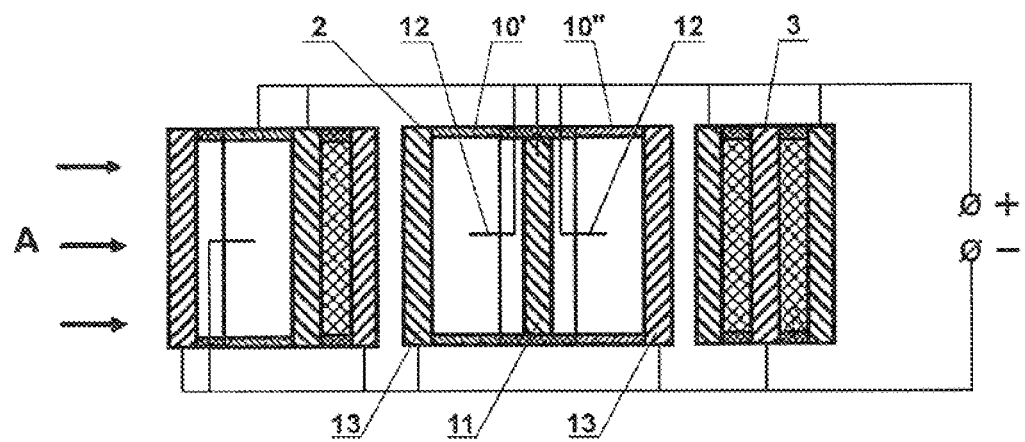
FIG. 2 is the same as FIG. 1, with the inactivation chamber wherein the needle electrodes of the first compartment and the second compartment are directed in opposite directions.

In the embodiment as shown in FIG. 2, unlike in that shown in FIG. 1, the needle corona electrodes 12 in the first compartment and the second compartment of the inactivation chamber 2 have their points directed in opposite directions and are electrically connected to the current-conductive partition 11. Herein, the corona electrodes 12 are connected to the pole of the power supply 4 opposite to the pole connected to the needle corona electrode 8 of the pretreatment means 1.

Figure 3:
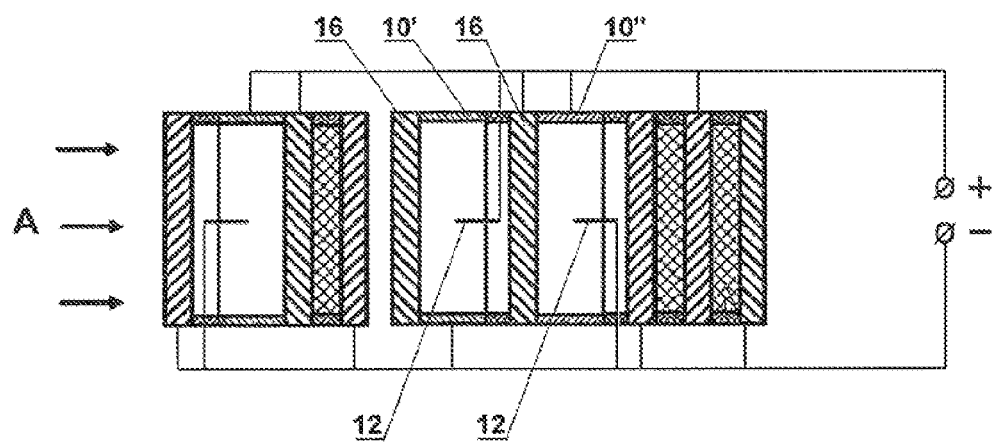
FIG. 3 is the same as FIG. 1, with the inactivation chamber wherein the needle electrodes of the first compartment and the second compartment are directed counterflow.

FIG. 3 shows the apparatus according to the invention with one more embodiment of the two-compartment inactivation chamber. In this embodiment, unlike in the two above-described embodiments, the two-compartment inactivation chamber is formed of two in-series arranged cylinder electrodes 10' and 10", wherein a plate 16 made of a permeable high-porosity current-conductive material is adjacent to the first end (along the flow) of each electrode. The cylinder electrodes 10' and 10" are connected to the opposite poles of the power supply 4. The needle corona electrodes 12 of the first compartment and the second compartment have their points directed counterflow and connected so that the electrode 12 of the first compartment is connected to the current-conductive plate 16 which is adjacent to the cylinder electrode of the second compartment and the needle electrode of the second compartment is connected to the current-conductive plate 14 of the precipitator 3 positioned directly following this electrode.

Figure 4:
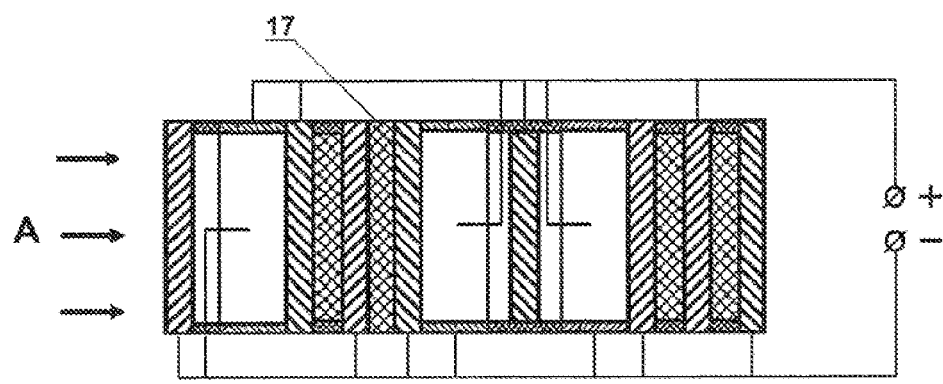
FIG. 4 is the same FIG. 2, but with an insulating plate positioned between the pretreatment means and the inactivation chamber.

The embodiment of the apparatus as shown in FIG. 4 is distinct from the embodiment shown in FIG. 2 in that it further comprises a plate 17 made of a permeable high-porosity (filtering) insulating material and installed between the second (along the flow) filtering unit of the pretreatment inactivation means 1 and the first compartment of the inactivation chamber 2.

Figure 5:
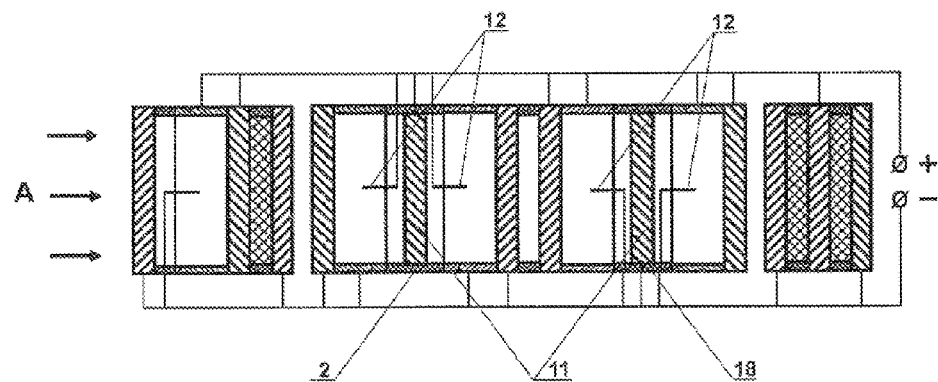
FIG. 5 shows an embodiment of the inactivation apparatus having two identical two-compartment inactivation chambers arranged in series to each other and having needle electrodes directed in opposite directions.

The apparatus shown in FIG. 5, as distinct from those described above, contains, apart from the two-compartment inactivation chamber 2, one more two-compartment chamber 18 installed in series to the chamber 2 along the air flow and having an analogous construction but with the opposite electrode connection polarity. In this embodiment, the needle corona electrodes 12 of the next chamber 18 are directed in the same way as the needle electrodes 12 of the previous chamber 2 (i.e., in opposite directions) and are electrically connected to each other and to the corresponding partition 11.

Figure 6:
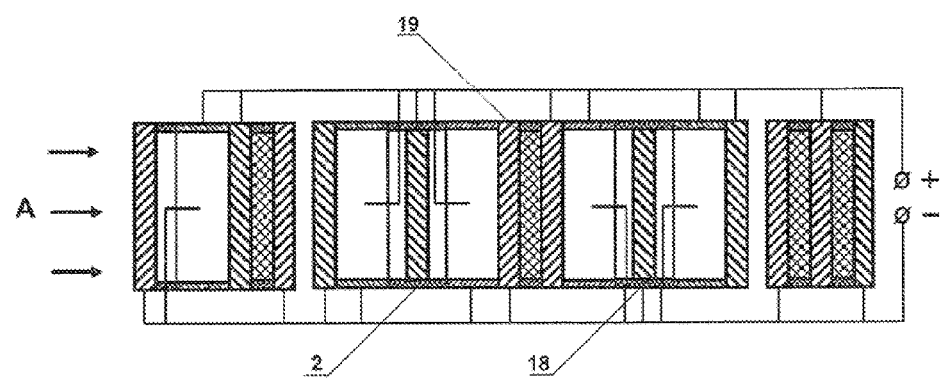
FIG. 6 is the same as FIG. 5, but with an insulating plate positioned between the inactivation chambers.

The embodiment of the apparatus as shown in FIG. 6 is distinct from the embodiment shown in FIG. 5 in that, between the neighboring inactivation chambers 2 and 18, there is further installed a plate 19 made of a permeable high-porosity insulating material, for example, open-cell foamed polyurethane.

The needle electrodes in the previous and next inactivation chambers may be directed in opposite directions; if so, however, the condition of the obligatory alternation of electrode connection polarity in each next chamber is also to be fulfilled.

Figure 7:
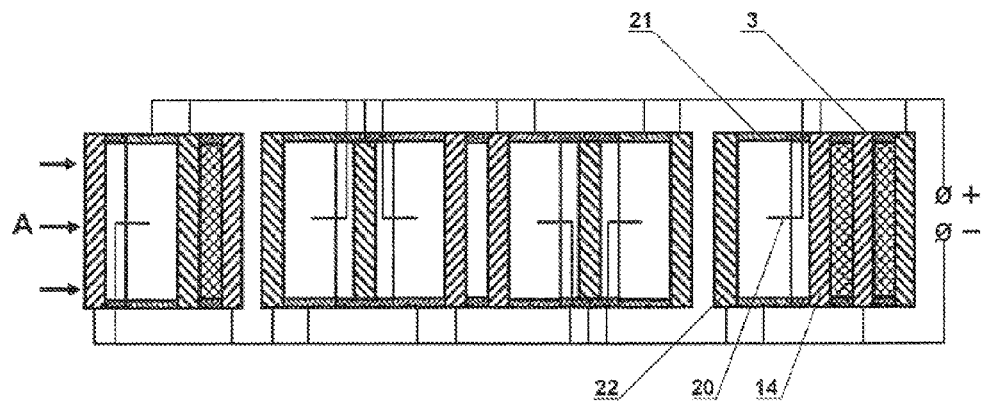
FIG. 7 shows an embodiment of the inactivation apparatus wherein the precipitator is further equipped with a corona unit.
Figure 8:
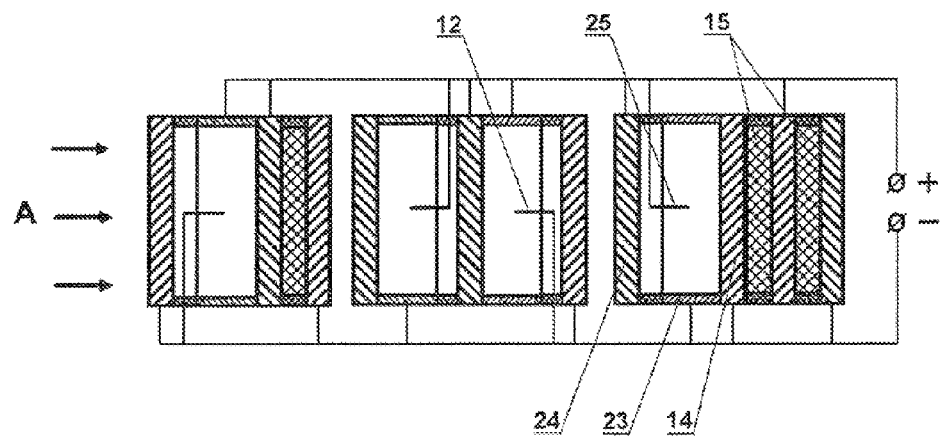
FIG. 8 is the same as FIG. 7, but with another embodiment of the precipitator.

The embodiments of the apparatus according to the invention as shown in FIGS. 7 and 8 are characterized in that the precipitator 3 is equipped with a needle-cylinder corona unit. In the embodiment of the inactivation apparatus as shown in FIG. 7, a needle electrode 20 is electrically connected to the first (along the flow) current-conductive plate 14 of the precipitator 3, this needle electrode having its point directed counterflow, and a cylinder non-corona electrode 21 is installed coaxially thereto, with a plate 22 made of a current-conductive filtering material being adjacent to the front end (along the flow) of the cylinder electrode and electrically connected to the needle electrodes 12 of the inactivation chamber 18.

In the embodiment of the apparatus as shown in FIG. 8, a cylinder electrode 23 is connected by its end to the first (along the flow) current-conductive plate 14 of the precipitator 3 and a plate 24 is installed across the flow opposite to the other end of the cylinder electrode 23, the plate 24 being followed by a needle corona electrode 25 installed coaxially to the cylinder electrode 23. The needle corona electrode 25 has its point directed along the flow, is electrically connected to the plate 24, and is connected to the pole of the power supply 4 opposite to the pole connected to the needle electrode 12 of the second compartment of the inactivation chamber 2.

The precipitator 3 is embodied in such a way that the separation between the current-conductive plates 14 decreases along the air flow A, wherein the current-conductive plates 14 are made of, for example, foamed nickel. The insulating plates 15 of the precipitator 3 are made of foamed polyurethane, wherein said plates are arranged so that the cell size of the material of the plates 15 decreases along the air flow A.

The cylinder electrodes 6, 10 (10' and 10"), 21, and 23 have a honeycomb (cellular) structure, wherein each of the needle electrodes 8, 12, 20, and 25 contains a plurality of needles, each needle being arranged coaxially to the corresponding cell.

Figure 9:
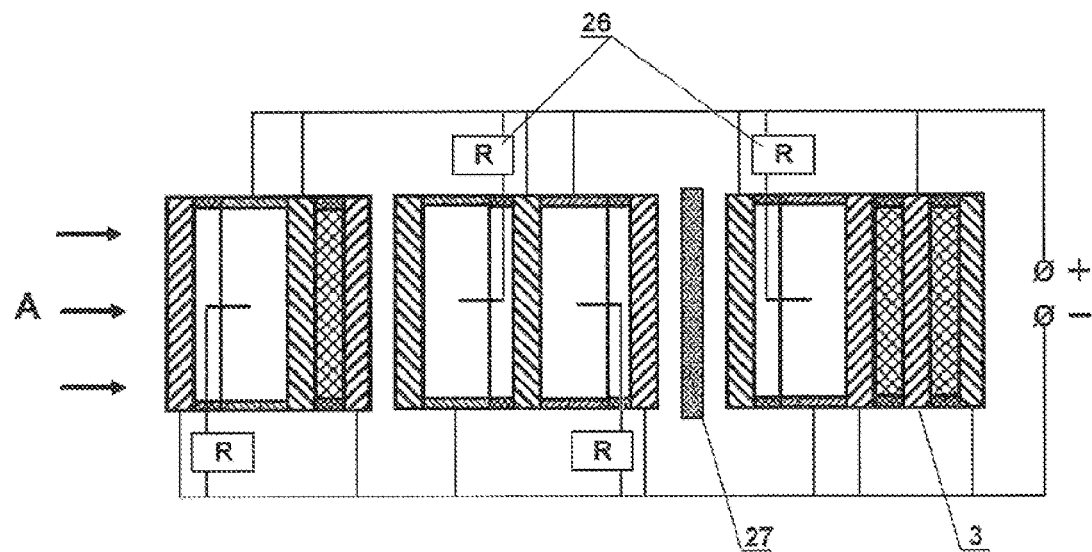
FIG. 9 shows an embodiment of the apparatus wherein the needle electrodes are connected to the power supply via resistors.

In the embodiment of the apparatus as shown in FIG. 9, each of the needle-cylinder corona units is embodied as a hollow cylinder and a single needle electrode which is positioned concentrically to the cylinder. Herein, each of the needle corona electrodes is connected to the power supply 4 via a high-voltage resistor 26, the resistance whereof being selected from the limit imposed on the peak consumption current value for the set voltage.

The precipitator 3 is preceded by a turbulizer 27, for example, having the perforated or bladed design, wherein the turbulizer 27 is equipped with a coating that contains a catalyst for catalyzing the decomposition of ozone, nitrogen oxide, and/or other harmful gases (for example, an alumina-based catalyst).

The high-voltage power supply 4 (FIG. 1) may be embodied as having three autonomous leads "a", "b", and "c". The lead "a" is connected to the needle corona electrodes and to the cylinder non-corona electrodes of the positive "coronas" of the apparatus; the lead "c" is connected to the needle corona electrodes and the cylinder non-corona electrodes of the negative "coronas;" and the lead "b" is connected to the current-conductive plates 14 of the precipitator or the current-conductive filtering units 7 and 7', having a plate made of an insulating filtering material installed between the filtering units. Herein, the power supply 4 is embodied in such a manner that the leads "a" and "c" are current stabilized and differ from each other in the voltage value and the lead "b" is voltage stabilized. Further, the power supply 4 in a preferred embodiment thereof is embodied with a feasibility of automatically switching its operation mode from voltage stabilization at the lead "b" to current stabilization once a set value of the consumed current is reached. Although this embodiment of the power supply is shown only in FIG. 1 which refers to the first embodiment of the invention, the same embodiment of the power supply is useful in other embodiments of the apparatus, too.

Figure 10:
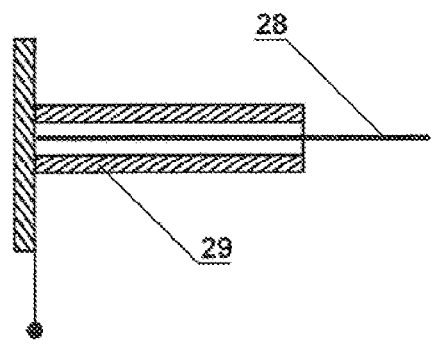
FIG. 10 shows an embodiment of a needle corona electrode in section.

FIG. 10 shows a section of the preferred embodiment of a needle corona electrode that represents a wire 28 mounted inside a metallic pipe 29 coaxially thereto and protruding therefrom by a value sufficient for an electrical corona to be formed.

In all embodiments of the apparatus, the non-corona electrodes may be embodied not only as cylinders but also as polyhedra or honeycombs.

The apparatus operates as follows.

The air to be treated contains various types of microorganisms, viruses, and particles having various sizes, structures, properties, and electrical charges.

Once a voltage is applied to electrodes, a corona current appears in the corona units of the apparatus, accompanied by the generation of the corresponding ions from the needle corona electrodes 8 and 12 (FIG. 1). Under the action of the ions generated, inside the pretreatment means 1 bioaerosols are charged and impacted by electrical fields of various strengths and gradients depending on the site where particles reside inside the pretreatment means 1. Cold plasma appears at the point of the needle corona electrode 8 and also has a local impact on bioaerosols. In the first (along the air flow) permeable porous electrode (plate 9), coarse filtration occurs to scavenge coarse particles. While the treated air flow is passing through the corona unit of the pretreatment means 1, microorganisms and viral cells first are charged by ions of one sip (for example, negative ions) and then pass through the porous base 7 of the non-corona electrode 6, which has the opposite potential sign, therein acquiring opposite charges. Then, while passing through the polarized structure of the insulating plate 5, microorganism and viral cells lose part of water from their surfaces in contact with this plate, thereby facilitating subsequent impact of electric fields and ions on the cellular structure, after which the cells change their charges upon passing through the second plate of the current-conductive filtering unit of the pretreatment means 1. Thereby provided are in fact identical electrical charge signs and weakened cellular structures of the microorganisms and viruses entering subsequent treatment. The embodiment of the first current-conductive filtering unit of the pretreatment means 1 as a needle-cylinder corona unit enables:

- improving the conditions for aerosol precipitating on the surface of the plate 5 made of a high-porosity insulating material and enhancing the efficiency of the surface dehydration of a microbial cell, wherein directing the point of the corona electrode 8 toward this plate 5 provides bioaerosol charging and simultaneously creates better conditions for the operation of the point of the needle;
- homogenizing the electrical potential of the bioaerosol contained in the air flow under treatment;
- weakening or partially damaging cellular membranes on account of a change in their surface signs and local structural deformations caused by varying electrical field gradients inside the pretreatment means, thereby considerably easing the subsequent disintegration of the cellular structure.

Leaving the pretreatment means 1, the bioaerosol-containing air flow enters the two-compartment inactivation chamber 2 which is equipped with two homopolar (FIGS. 1 and 2) or heteropolar (FIG. 3) corona electrodes 12.

Inside the two-compartment inactivation chamber 2 in a permanent electrical field having locally variable strengths and gradients, the bioaerosol is multiply recharged under the impact of ions, electrical contact with electrodes of opposite signs, and the surface of the polarized insulating filtering material. This impact results in the deformation or local damage of the cellular structure and the alteration of the mechanical, electrical, and other properties of the deformed material (for example, the dielectric constant of the membrane material changes), which induces the disintegration of the cellular structure and the inactivation of microorganisms. Having passed through the inactivation chamber 2, the microorganisms and viruses suspended in the air flow are in an inactivated state.

The embodiments of the inactivation chamber 2 as shown in FIGS. 1, 2, and 3 differ from one another, in fact, only in the geometry of variation of the electrical field strength and gradients along the flow and across the cross-sectional area thereof and, as a result, in the travel direction and velocity of ions, thereby allowing the selection of the inactivation chamber design proceeding from the parameters of the air flow to be inactivated (the flow velocity, the type of aerosol, the physical parameters of the components thereof, and the like).

On account of the fact that after passing through the air flow pretreatment means 1, bioaerosol particles enter the inactivation chamber 2 having essentially equal charges and being partially deformed and damaged, the ultimate disintegration of the cellular structure of microorganisms inside the inactivation chamber 2 occurs with a higher efficiency.

The embodiments of the apparatus as shown in FIGS. 5 and 6 provide a further enhancement of the inactivation effect and an increase in the air flow treatment rate, as well as an improvement of the reliability of the apparatus; these embodiments comprise, apart from the two-compartment inactivation chamber 2, at least one more two-compartment inactivation chamber 18 installed next to the first chamber in series along the flow which is an analogue of the first chamber but has the opposite polarity of electrode connection. Herein, the direction of the needle corona electrodes (12) of each next inactivation chamber is identical or opposite to the direction of the needle electrodes of the previous one. This embodiment provides an additional effect by an increased number of electrode polarity alternations and an increased time of impact of opposite-polarity fields on the bioaerosol.

The plate 17 (FIG. 4), which is made of a high-porosity insulating material and installed between the second filtering unit of the pretreatment means 1 and the first compartment of the inactivation chamber 2, provides an enhanced efficiency of aerosol dehydration by allowing an additional precipitation of bioaerosol particles on the surface thereof.

An analogous plate 19 (FIG. 6) made of a high-porosity insulating material and installed between the neighboring current-conductive filtering plates 13 of the previous and next inactivation chambers (2 and 18, respectively) also offers an additional depolarized surface for bioaerosol particles to precipitate.

After passing the inactivation chambers 2 and 18 and acquiring a charge sufficient for precipitation, the particles enter the precipitator 3 together with the air flow A (FIGS. 7, 8). Herein, the inactivated particles suspended in the air flow precipitate on the plates 14 and 15 of the precipitator 3. Inasmuch as the bioaerosol particle charge is unsteady after the flow A passes the inactivation chambers 2 and 18 and depends on a number of uncontrollable factors (the electrical properties of particles, the condition of corona and non-corona electrodes, air humidity, the air flow rate, and some others), for improving the efficiency of fine filtration and for providing the required degree of air ionization the precipitator 3 (FIG. 7) is equipped with a needle-cylinder corona unit wherein the needle electrode 20 is directed counter the flow A, or with a corona unit wherein the cylinder 23 bearing needle electrode 25 is directed along the flow A (FIG. 8). After microorganisms and viruses are inactivated in the inactivation chambers 2 and 18, the air flow can contain nonliving particles of microbial cells or their fragments, viruses, aerosols, and other species having sizes of up to 0.08 µm, which may be undesirable. The corona unit installed at the inlet of the precipitator 3 enhances scavenging of the aforementioned particles from the treated flow. The flow turbulizer 27, which is installed in this embodiment upstream of the precipitator 3, enhances the elimination of the nonuniformity of cross-sectional distribution of concentrations of ions, particles, ozone, and other species, this nonuniformity arising from use of more than one corona units in parallel in the apparatus.

The catalytic coating of the turbulizer, as the presence of a suitable catalyst for catalyzing the decomposition of ozone, nitrogen oxide, and/or other harmful gases in the material of the insulating filtering plates 15 of the precipitator 3, too, provides a decrease in concentrations of ozone, nitrogen oxides, and other admixed harmful gases.

The power supply 4 embodied as being capable of stabilizing the voltage value and maintaining the consumption current value within the set range, provides the possibility of controlling the course of the inactivation process with limited ozone generation by the corona units.

The high-voltage resistors 26 (FIG. 9), the resistance whereof is selected from the limit imposed on the peak consumption current value for the set voltage, installed between each needle corona electrode and the power supply 4, provide uniform current distribution over the corona units of the apparatus.

The permeable porous electrodes have a three-dimensional structure, for example, the structure of an open-cell material (foamed nickel, foamed copper, and others).

The needle corona electrodes embodied as the wire 28 installed inside the metallic pipe 29 coaxially thereto, as shown in FIG. 10, are characterized by high construction strengths (vibration strength and impact strength).

The arrangement of the current-conductive plates 14 of the precipitator 3 with the separation between them decreasing along the air flow, promotes the increase in the electric field strength between the neighboring permeable porous electrodes (current-conductive plates) along the flow. Thereby improved is the filtration efficiency at each next filtering unit, as a result providing an enhancement of the overall efficiency of filtration and the life of the precipitator.

The decreasing cell sizes in the material of the insulating plates 15 of the precipitator 3 along the flow A enhance an increase in the efficiency of fine particle filtration in the treated air flow.

The invention claimed is:

1. An apparatus for the inactivation and fine filtration of viruses and microorganisms in an air flow comprising a high-voltage power supply (4) and, in series along the air flow: an air flow pretreatment means (1) formed of oppositely charged current-conductive filtering units (7, 7') with a plate (5) made of a permeable high-porosity insulating material installed between the filtering units; a two-compartment inactivation chamber (2), each compartment whereof being embodied as a needle corona electrode (12) and a cylinder non-corona electrode (10) arranged coaxially to each other and each being electrically connected to the corresponding plate (13) made of a current-conductive filtering material; and a precipitator (3) embodied as oppositely charged plates (14) arranged in parallel to each other and made of a high-porosity current-conductive material, with plates (15) between them made of a permeable high-porosity insulating material, the apparatus being characterized in that: at least the first (along the air flow) current-conductive filtering unit (7) of the pretreatment means (1) is embodied as a cylinder electrode (6) having a base in the form of a plate (7) made of a permeable porous current-conductive material and positioned adjacent to the plate (5), which is made of a permeable high-porosity insulating material, and a plate (9), which is made of a high-porosity current-conductive material, arranged at a distance from the free end of the cylinder electrode, and to which adjacent is a needle electrode (8), the electrode 8 being electrically connected to the plate (9), being arranged coaxially to the cylinder electrode (6), and having its point directed toward the insulating plate (5), wherein the cylinder electrode (6) and the needle electrode (8) are connected to the opposite poles of the power supply (4).

2. The apparatus according to claim 1, characterized in that the two-compartment inactivation chamber (2) is embodied as a single cylinder non-corona electrode (10), inside which a partition (11) made of a permeable high-porosity current-conductive material is installed across the flow, a plate (13) made of a current-conductive filtering material is arranged opposite to each of the free ends of the cylinder non-corona electrode, and the needle corona electrodes (12) of the first compartment and the second compartment have their points directed toward each other and are electrically connected to each other and to the corresponding plate (13), wherein the needle corona electrodes (12) of the first compartment and the second compartment are connected to the pole of the power supply (4) that is opposite to the pole connected to the needle electrode (8) of the pretreatment means (1).

3. The apparatus according to claim 1, characterized in that the needle corona electrodes (12) of the first compartment and the second compartment of the two-compartment inactivation chamber (2) have their points directed in opposite directions and are installed coaxially to the corresponding cylinder electrodes (10', 10') on the opposite sides of the partition (11') which is made of a current-conductive filtering material, positioned across the flow between the cylinder non-corona electrodes (10', 10") of the first compartment and the second compartment, and insulated from them, wherein the plates (13) made of a current-conductive filtering material and positioned adjacent to the ends of the cylinder electrodes at the inlet and the outlet of the inactivation chamber (2) arc electrically connected to each other and to the last (along the flow) current-conductive filtering plate (7) of the pretreatment means (1) and wherein the needle corona electrodes (12) are electrically connected to the partition (11') made of a current-conductive filtering material and arranged between them.

4. The apparatus according to claim 1, characterized in that the two-compartment inactivation chamber (2) is formed of two in-series arranged cylinder non-corona electrodes (10', 10"), a plate (16) made of a current-conductive filtering material being adjacent to the first (along the flow) end of each electrode, wherein the non-corona electrodes (10', 10") are connected to the opposite poles of the power supply (4) and wherein the needle corona electrodes (12) have their points directed counterflow, the needle electrode (12) of the first compartment of the chamber being electrically connected to the current-conductive plate (16) that is adjacent to the cylinder electrode (10") of the second compartment and the needle electrode (12) of the second compartment of the inactivation chamber (2) being electrically connected to a plate made of a current-conductive filtering material and arranged immediately following this electrode.

5. The apparatus according to claim 2, characterized in that a plate (17) made of an insulating filtering material is installed between the second (along the flow) filtering unit (7') of the pretreatment means (1) and the first compartment of the inactivation chamber (2).

6. The apparatus according to claim 5, characterized in that it further contains at least one more two-compartment inactivation chamber (2), which is an analogue of the first chamber but has the opposite polarity of electrode connection, installed in series to the first chamber along the flow, wherein the direction of the needle corona electrodes (12) of each next chamber is identical or opposite to the direction of the needle electrodes (12) of the previous one.

7. The apparatus according to claim 6, characterized in that a plate (19) made of a high-porosity insulating material is installed between the neighboring current-conductive filtering plates (13) of the previous and next inactivation chambers (2).

8. The apparatus according to claim 7, characterized in that a needle electrode (20) is electrically connected to the first (along the flow) current-conductive plate (14) of the precipitator (3), the electrode (20) having its point directed counterflow, and in that a cylinder non-corona electrode (21) is installed coaxially to the electrode (20) and a plate (22) made of a current-conducting filtering material is adjacent to the front (along the flow) end of the electrode (21) and is electrically connected to the needle electrodes (12) of the last (along the flow) inactivation chamber (2).

9. The apparatus according to claim 7, characterized in that a cylinder electrode (23) is connected by an end thereof to the first (along the flow) current-conductive plate (14) of the precipitator (3), an additional plate (24) made of a current-conductive filtering material is installed across the flow opposite to the other end of the cylinder electrode (23), wherein a needle corona electrode (25) is positioned coaxially to the cylinder electrode (23), has the point thereof directed along the flow, is electrically connected to said additional plate (24), and is connected to the pole of the power supply (4) opposite to the pole connected to the needle electrode (12) of the last compartment of the inactivation chamber (2).

10. The apparatus according to claim 6, characterized in that it is equipped with at least one flow turbulizer (27) that is capable of leveling the concentrations of particles to be precipitated, ozone, or ions in the flow.

11. The apparatus according to claim 10, characterized in that the flow turbulizer (27) is installed upstream of the precipitator (3).

12. The apparatus according to claim 11, characterized in that at least one of the current-conductive plates (14) of the precipitator (3) and/or the turbulizer (27) are equipped with a coating that is capable of providing the decomposition of ozone, nitrogen oxide, and/or other harmful gases.

13. The apparatus according to claim 8, characterized in that the material of the insulating filtering plates (15) of the precipitator contains a catalyst for catalyzing the decomposition of ozone, nitrogen oxides, and/or other noxious gases.

14. The apparatus according to claim 1, characterized in that the needle corona electrode (12) is embodied as a wire (28) installed inside a metallic pipe (29) coaxially thereto and protruding therefrom.

15. The apparatus according to claim 8, characterized in that at least one of the corona electrodes (8, 12, 20, and 25) is connected to the power supply via a resistor (26), the resistance value whereof is selected from the limit imposed on the peak consumption current for the set voltage.

16. The apparatus according to claim 1, characterized in that the high-voltage power supply (4) is embodied as having three autonomous leads (a, b, and c), wherein one lead (b) is connected to the current-conductive plates (14) of the precipitator and to the current-conductive filtering units (7, 7) and voltage-stabilized and the other two leads (a and c) are respectively connected to the needle corona electrode (8 or 12) and the cylinder non-corona electrode (6 or 10) of each respective compartment and are current-stabilized.

17. The apparatus according to claim 16, characterized in that the high-voltage power supply (4) is embodied with a feasibility of automatically switching the operation mode thereof from the voltage stabilization of the lead connected to the current-conductive plates (14) of the precipitator and to the current-conductive filtering units (7, 7), to current stabilization once a set value of the consumption current is reached.

18. The apparatus according to claim 1, characterized in that the current-conductive plates (14) of the precipitator are made of a foamed metal and in that the separation between them decreases along the air flow.

19. The apparatus according to claim 1, characterized in that the insulating filtering plates (15) of the precipitator are made of foamed polyurethane, wherein the cell size of the material of the plates decreases along the air flow.

20. The apparatus according to claim 1, characterized in that the current-conductive plates (14) of the precipitator are made of a foamed metal coated with an insulating coating.

\* \* \* \* \*